US00PP29176P3

(12) United States Plant Patent
Volmary

(10) Patent No.: US PP29,176 P3
(45) Date of Patent: Apr. 3, 2018

(54) ***VERBENA* PLANT NAMED 'VOLVER 7551'**

(50) Latin Name: *Verbena×peruviana*
Varietal Denomination: VOLVER 7551

(71) Applicant: Hubertus Volmary, Muenster (DE)

(72) Inventor: Hubertus Volmary, Muenster (DE)

(73) Assignee: Volmary GmbH, Muenster (DE)

( * ) Notice: Subject to any disclaimer, the term of this patent is extended or adjusted under 35 U.S.C. 154(b) by 4 days.

(21) Appl. No.: 14/999,186

(22) Filed: Apr. 8, 2016

(65) Prior Publication Data

US 2017/0295693 P1 Oct. 12, 2017

(51) Int. Cl.
*A01H 5/02* (2006.01)

(52) U.S. Cl.
USPC ..... Plt./308
CPC ..... *A01H 5/02* (2013.01)

(58) Field of Classification Search
USPC ..... Plt./308
See application file for complete search history.

*Primary Examiner* — Keith O Robinson
(74) *Attorney, Agent, or Firm* — C. A. Whealy

(57) ABSTRACT

A new and distinct cultivar of *Verbena* plant named 'VOLVER 7551', characterized by its compact and trailing plant habit; moderately vigorous growth habit; freely branching habit; freely flowering habit; and inflorescences of with purple and light pink bi-colored flowers that are held above and beyond the foliar plane on strong peduncles.

1 Drawing Sheet

Botanical designation: *Verbena×peruviana*.
Cultivar denomination: 'VOLVER 7551'.

BACKGROUND OF THE INVENTION

The present invention relates to a new and distinct cultivar of *Verbena* plant, botanically known as *Verbena×peruviana*, and hereinafter referred to by the name 'VOLVER 7551'.

The new *Verbena* plant is a product of a planned breeding program conducted by the Inventor in Muenster, Germany. The objective of the breeding program is to create new trailing and freely-branching *Verbena* plants with numerous large attractive flowers.

The new *Verbena* plant originated from an open-pollination in 2013 in Muenster, Germany of an unnamed proprietary selection of *Verbena×peruviana*, not patented, as the female, or seed, parent with an unknown selection of *Verbena×peruviana* as the male, or pollen, parent. The new *Verbena* plant was discovered and selected by the Inventor as a flowering plant from within the progeny of the stated open-pollination in a controlled greenhouse environment in Muenster, Germany in 2014.

Asexual reproduction of the new *Verbena* plant by terminal cuttings in a controlled environment in Muenster, Germany since 2015 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'VOLVER 7551'. These characteristics in combination distinguish 'VOLVER 7551' as a new and distinct *Verbena* plant:

1. Compact and trailing plant habit.
2. Moderately vigorous growth habit.
3. Freely branching habit.
4. Freely flowering habit.
5. Inflorescences of with purple and light pink bi-colored flowers that are held above and beyond the foliar plane on strong peduncles.

Plants of the new *Verbena* can be compared to plants of the female parent selection. Plants of the new *Verbena* differ primarily from plants of the female parent selection in the following characteristics:

1. Plants of the new *Verbena* are more compact and denser than plants of the female parent selection.
2. Plants of the new *Verbena* are not as upright as and are more trailing than plants of the female parent selection.
3. Plants of the new *Verbena* and the female parent selection differ in flower color as plants of the female parent selection have solid purple-colored flowers.

Plants of the new *Verbena* can be compared to plants of the *Verbena hybrida* 'VEAZ0016', disclosed in U.S. Plant Pat. No. 25,665. In side-by-side comparisons conducted in Muenster, Germany, plants of the new *Verbena* differ primarily from plants of 'VEAZ0016' in the following characteristics:

1. Plants of the new *Verbena* are more compact than plants of 'VEAZ0016'.
2. Plants of the new *Verbena* are not as mounding as and are more trailing than plants of 'VEAZ0016'.
3. Plants of the new *Verbena* and 'VEAZ0016' differ in flower color as plants of 'VEAZ0016' have red-colored flowers with white-colored centers.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the actual colors of the new *Verbena* plant.

The photograph is a side perspective view of a typical flowering plant of 'VOLVER 7551' grown in a container.

DETAILED BOTANICAL DESCRIPTION

The aforementioned photograph and following observations and measurements describe plants grown during the spring in 12-cm containers in a glass-covered greenhouse in Muenster, Germany and under commercial practices typical of commercial *Sutera* production. During the production of the plants, day temperatures ranged from 18° C. to 25° C., night temperatures ranged from 15° C. to 18° C. and light levels ranged from 5 to 65 klux. Plants were pinched two to three weeks after planting and were six months old when the photograph and the description were taken. In the following description, color references are made to The Royal Horticultural Society Mini Colour Chart, 2005 Edition, except where general terms of ordinary dictionary significance are used.

Botanical classification: *Verbena×peruviana* 'VOLVER 7551'.

Parentage:

*Female, or seed, parent*.—Unnamed proprietary selection of *Verbena×peruviana*, not patented.

*Male, or pollen, parent*.—Unknown selection of *Verbena×peruviana*, not patented.

Propagation:

*Type*.—By terminal cuttings.

*Time to initiate roots, summer*.—About one to two weeks at temperatures ranging from about 20° C. to 25° C.

*Time to initiate roots, winter*.—About two to three weeks at temperatures ranging from about 15° C. to 23° C.

*Time to produce a rooted young plant, summer*.—About three weeks at temperatures ranging from about 20° C. to 25° C.

*Time to produce a rooted young plant, winter*.—About 30 days at temperatures ranging from about 15° C. to 23° C.

*Root description*.—Fine, fibrous.

*Rooting habit*.—Freely branching; medium density.

Plant description:

*Plant and growth habit*.—Compact and trailing plant habit; moderately vigorous growth habit.

*Plant height*.—About 18 cm.

*Plant diameter* (*spread*).—About 66 cm.

Lateral branch description:

*Branching habit*.—Freely branching habit with about 19 lateral branches developing per plant; pinching enhances lateral branch development.

*Length*.—About 30 cm.

*Diameter*.—About 3 mm to 5 mm.

*Internode length*.—About 1 cm. to 1.8 cm.

*Strength*.—Strong.

*Texture*.—Pubescent.

*Color*.—Close to 144A.

Leaf description:

*Arrangement*.—Opposite, simple.

*Length*.—About 2.8 cm to 5.4 cm.

*Width*.—About 1.8 cm to 3.5 cm.

*Shape*.—Elliptic; not divided.

*Apex*.—Acute.

*Base*.—Attenuate.

*Margin*.—Dentate.

*Texture, upper and lower surfaces*.—Pubescent; pilose.

*Venation pattern*.—Pinnate.

*Color*.—Developing leaves, upper surface: Close to 136A. Developing leaves, lower surface: Close to 137A. Fully expanded leaves, upper surface: Close to 136A; venation, close to 142D. Fully expanded leaves, lower surface: Close to 137C; venation, close to 142D.

*Petioles*.—Length: About 3 mm to 5 mm. Diameter: About 3 mm. Texture: Densely pilose. Color: Close to 144C.

Flower description:

*Flower arrangement and habit*.—Sessile salverform flowers arranged in terminal hemispherical umbels; flowers face upward to somewhat outwardly; freely flowering habit with about 11 to 14 flowers per inflorescence with numerous inflorescences developing per plant during the flowering season.

*Natural flowering season*.—Plants flower continuously from throughout the summer in Germany; early flowering habit, plants begin flowering about ten to twelve weeks after planting.

*Flower longevity*.—Flowers last about six days on the plant; flowers persistent.

*Fragrance*.—None detected.

*Inflorescence diameter*.—About 7 cm to 8 cm.

*Inflorescence height*.—About 4 cm.

*Flower diameter*.—About 2.5 cm.

*Flower depth* (*height*).—About 1.5 cm.

*Throat diameter*.—About 2.6 cm.

*Tube length*.—About 2.1 cm.

*Tube diameter, proximally*.—About 2 mm.

*Flower buds*.—Length: About 8 mm to 10 mm. Diameter: About 2 mm. Shape: Elongated to ovate. Color: Close to 137A.

*Corolla*.—Arrangement: Single whorl of five adjacent petals fused towards the base into a narrow straight tube. Petal lobe length: About 2.5 cm. Petal lobe width: About 1.5 cm. Petal lobe shape: Roughly cordate. Petal lobe apex: Emarginate. Petal margin: Entire. Petal texture, upper and lower surfaces: Pilose. Petal luster, upper surface: Slightly glossy. Petal luster, lower surface: Matte. Throat texture and luster: Smooth, glabrous; slightly glossy. Tube texture and luster: Smooth, glabrous; glossy. Color: Petal, when opening and fully opened, upper surface: Close to 185B; towards the margins, close to 65B; throat, close to 65B and 138D. Petal, when opening and fully opened, lower surface: Close to 184D; towards the margins, close to 65B; tube, close to 138D.

*Calyx*.—Arrangement: Single whorl of five fused sepals fused towards the base into a narrow tube. Sepal length: About 1 cm. Sepal width: About 2 mm. Sepal shape: Lanceolate. Sepal apex: Acuminate. Sepal margin: Entire. Sepal texture, upper and lower surfaces: Pilose, slightly rough. Sepal color: When developing, upper surface: Close to 143A. When developing, lower surface: Close to between 143A and 136B. Fully developed, upper and lower surfaces: Close to between 143A and 136B.

*Peduncles*.—Length: About 7.5 cm. Diameter: About 2 mm to 3 mm. Strength: Strong. Texture: Pilose; rough. Color: Close to 145A.

*Reproductive organs*.—Stamens: Quantity per flower: Four. Filament length: About 2 mm to 3 mm. Filament color: Close to 144D. Anther shape: Ovoid. Anther length: About 1 mm. Anther color: Close to 144D. Pollen amount: Moderate. Pollen color: Close to 154D. Pistils: Quantity: One per flower. Pistil length: About 2 cm to 2.3 cm. Stigma shape: Biparted. Stigma color: Close to 144C. Style length: About 1.8 cm. Style color: Close to 144C. Ovary color: Close to 144C.

*Fruits and seeds*.—Fruit and seed development have not been observed on plants of the new *Verbena*.

Garden performance: Plants of the new *Verbena* have been observed to have good garden performance and to tolerate wind, rain and temperatures ranging from about 4° C. to about 36° C.

Pathogen & pest resistance: Plants of the new *Verbena* have been observed to have good resistance to Powdery Mildew (*Erysiphe cichoracearum*). Plants of the new *Verbena* have not been observed to be resistant to pests and other pathogens common to *Verbena* plants.

It is claimed:

1. A new and distinct *Verbena* plant named 'VOLVER 7551' as illustrated and described.

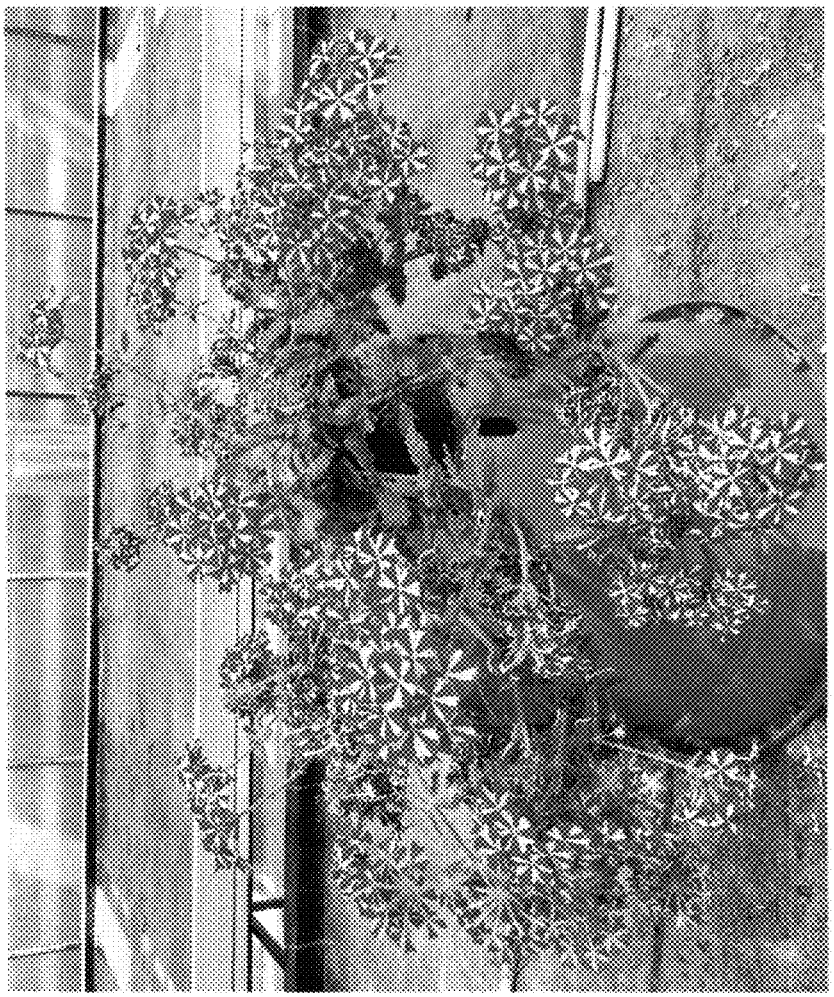

* * * * *